(12) United States Patent
Radatti et al.

(10) Patent No.: US 7,793,836 B2
(45) Date of Patent: *Sep. 14, 2010

(54) MEDICINE MANAGEMENT METHODS AND APPARATUS

(75) Inventors: Peter V. Radatti, Conshohocken, PA (US); Marie D. Radatti, Conshohocken, PA (US)

(73) Assignee: CyberSoft, Inc., West Conshohocken, PA (US)

( * ) Notice: Subject to any disclaimer, the term of this patent is extended or adjusted under 35 U.S.C. 154(b) by 26 days.

This patent is subject to a terminal disclaimer.

(21) Appl. No.: 12/152,278

(22) Filed: May 13, 2008

(65) Prior Publication Data

US 2009/0050694 A1     Feb. 26, 2009

Related U.S. Application Data

(63) Continuation-in-part of application No. 11/104,330, filed on Apr. 12, 2005, now Pat. No. 7,370,795.

(51) Int. Cl.
*G06F 7/08*     (2006.01)
*G06F 17/00*    (2006.01)
*G06F 19/00*    (2006.01)
*G06Q 10/00*    (2006.01)

(52) U.S. Cl. .............. 235/381; 235/375; 235/385; 705/28

(58) Field of Classification Search ............ 235/375, 235/381, 385, 462.01; 705/28
See application file for complete search history.

(56) References Cited

U.S. PATENT DOCUMENTS

| 7,370,795 | B2 * | 5/2008 | Radatti et al. ............ 235/381 |
| 2003/0099158 | A1 * | 5/2003 | De la Huerga ............ 368/10 |
| 2004/0172163 | A1 * | 9/2004 | Varis ........................ 700/237 |
| 2004/0182873 | A1 * | 9/2004 | Baum ........................ 221/15 |
| 2005/0041531 | A1 * | 2/2005 | Sekura ....................... 368/10 |
| 2005/0109658 | A1 * | 5/2005 | Bindford .................... 206/534 |

* cited by examiner

*Primary Examiner*—Thien Minh Le
*Assistant Examiner*—April A Taylor
(74) *Attorney, Agent, or Firm*—John F. A. Earley, III; Frank J. Bonini, Jr.; Harding, Earley, Follmer & Frailey, P.C.

(57) ABSTRACT

Methods and apparatus are shown for providing information on a pill. A patient specific delivery apparatus for medicine using information on a pill or pills is shown as well, and a database with patient specific information may be provided, resulting in an individualized pharmacopoeia for a patient. A dispenser and a method for dispensing pills are provided and may generate audible messages. The dispenser may be constructed with a protective barrier to maintain shelf-life and integrity of the pills.

43 Claims, 4 Drawing Sheets

MEDICINE MANAGEMENT METHODS AND APPARATUS

CROSS-REFERENCE TO RELATED APPLICATIONS

This application is a continuation-in-part of U.S. application Ser. No. 11/104,330 filed on Apr. 12, 2005, now U.S. Pat. No. 7,370,795, the complete disclosure of which is incorporated herein by reference.

BACKGROUND OF THE INVENTION

1. Field of the Invention

The present disclosure relates to medicine management. More particularly, the present disclosure relates to medicine management methods and apparatus.

2. Brief Description of the Related Art

Managing medicines may be crucial to the patient. For example, properly managing the taking of medicine, because of mistakes, forgetfulness, etc., may be problematic. As another example, medicine often must be taken according to a prearranged or predetermined schedule. Managing that schedule may be difficult, however, e.g., when a patient forgets to take his or her medicine, forgets when medicine was last taken, etc. Moreover, difficulties may be compounded when multiple medicines need to be taken, thus compounding management difficulties.

Other problems may arise in addition to management problems. For example, when multiple medicines are required, interactions between the medicines must be carefully considered, as medicines may interact with each other in less than desirable fashion, which may lead to serious, unintended consequences for the patient.

SUMMARY OF THE INVENTION

Methods and devices for managing medicine are provided. The methods and devices facilitate labeling and dosing, and provide improvements for managing medicine through labeling and coordination of information and pill packaging and alerting.

Embodiments of the invention provide devices and management for facilitating pill taking and dispensing through the generation of audible messages.

According to alternate embodiments, an improved pill container or dispenser is provided which has improved storing capabilities. Exemplary embodiments may include a barrier which minimizes the likelihood of or prevents potential spoiling contaminants, such as oxygen and other substances or vapors, including moisture, from penetrating the dispenser.

DETAILED DESCRIPTION OF THE INVENTION

Figure 1:
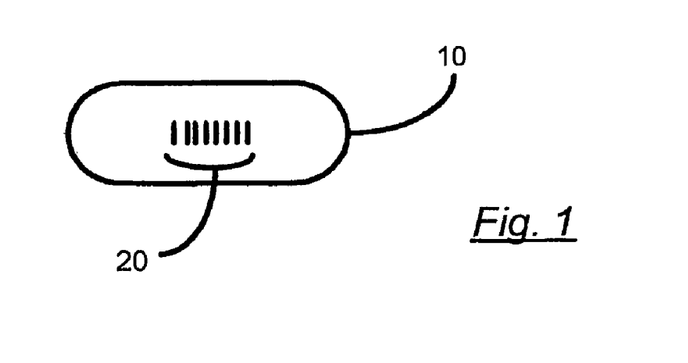
FIG. 1 shows a preferred embodiment.

FIG. 1 shows a preferred embodiment. A pill 10 is shown. Information 15 is present upon the pill.

The word "pill" is used herein to indicate a delivery system for a medicine.

The word "medicine" is used herein to include materials for diagnosing, treating, and/or preventing disease and/or other damage to a patient (including drugs, any other suitable substances, etc.,) and/or materials for supporting and/or maintaining health of a patient (including but not limited to supplements (including dietary supplements,) nutrients, vitamins, minerals, any other suitable substances, etc.)

"Delivery" is used herein to indicate the process of taking medicine.

"Delivery system" is used herein to indicate any type of delivery systems suitable for delivering medicine. For example, Oral Drug Delivery Systems, such as; Oral Controlled-Release Drug Delivery Systems, Tablets, Capsules, Coated Tablets and Capsules, Gel-Caps, Caplets, Diffusion Systems, Reservoir Systems, Chewable Tablets, Rapid Dissolving Systems, Buccal Systems, Effervescent Systems, Polymer-Based Systems, etc.; Parenteral Drug Delivery Systems, such as, Infusion Products, Supplies and Devices, IV Administration Sets, Pumps, Controllers, and Catheters, Hypodermic Products, Supplies and Devices, such as Syringes, Needles, etc., Specialized Parenteral Dosage Formulations, such as Monoclonal Antibodies, Polymers, Liposomes, Hemodialysis Products, Peritoneal Dialysis Products, Enteral Feeding Products, etc.; Inhalation Drug Delivery Systems, such as Dry Powder Inhalers, Metered Dose Inhalers, Nasal Spray Dispensers, Liquid Inhalers, Inhalation Supplies and Devices, Oxygen Therapy Equipment, Oxygen Therapy Supplies, Ventilators, Anesthesia Equipment, Anesthesia Disposables, Nebulizers, etc.; Transmucosal, Transdermal and Implantable Drug Delivery Systems, such as Transdermal Drug Delivery Systems, Transdermal Technologies, e.g., Estrogen Replacement Patches, Nicotine Patches, etc.; Implantable Drug Delivery Systems, such as Pulse Generators, Drug Inserts, Drug-Eluting Stents, etc.; Organ System Specific Drug Delivery, such as Pulmonary Drug Delivery, Nasal Delivery to Central Nervous System, Cardiovascular System, Gastro-Intestinal Tract, Genito-Urinary Tract, Ocular Drug Delivery, Controlled Release Systems, etc.; Highly Targeted Drug Delivery Systems, such as Polymer and Collagen Systems, Particle-Based Systems, Therapeutic Monoclonal Antibodies, Liposomes, Microparticles, Modified Blood Cells, Nanoparticles, Viral Assisted Intracellular Gene Delivery, Non-Viral Intracellular Gene Delivery, etc.

"Patient" is used to indicate the organism to be treated (including but not limited to human, non-human animal, any other suitable organism, etc.)

Returning now to the embodiment of FIG. 1, information 15 may be as varied as desired, as is further described below. In preferred embodiments, information 15 contains the name of the medicine (which may be scientific, generic or manufacturer specific,) the dosage embodied in the pill, lot number, serial number, and manufacturer name, printed on pill 10 in coded form. Embodiments may provide pill specific information, which is defined herein as the name of the medicine, size and/or dosage of the medicine.

The coded form used in the embodiment of FIG. 1 is bar coding. Thus, the information is readable by a bar code reader.

The bar coding scheme of preferred embodiments may use predetermined coding, e.g., a numerical designation assigned to a manufacturer, a numerical designation for the name of the medicine, etc.

Information present on pills may vary as desired in various embodiments. For example, generic and/or specific information may be used. An example of generic information is information that is of interest to or about more than one specific patient, such as manufacturer name, scientific names and/or formulas, etc. An example of patient specific information is information that is of interest to or about a specific patient such as physician information, information about medical conditions, etc.

Information may be generic as well as patient specific, that is, could be present in a generic form and/or be modified to be in a patient specific form. Examples of information that may be either or both generic and patient specific are: use and/or instructional information, such as dosages, known interactions, limits, etc.; scheduling information, etc.

Information may be used as well that is already present on a pill. For example, weight, color, shape, or other suitable indicia may be used in combination with added information.

Returning to FIG. 1, in the embodiment therein, information 15 is printed on pill 10 in any suitable ink, e.g., edible soy inks, etc. In other embodiments, engraving, or any other suitable means, may be used as desired to mark a pill with desired information. For example, laser or other suitable means; masking means; ion deposit means; light wave or other electromagnetic reflection and/or refraction means which may include surface modification means; or any other suitable means. More than one marking mechanism may be used as well, as is further described below.

Marking means do not have to be exclusively external, but may also be any suitable internal means, such as doping with appropriate inert substances that suitably reflect electromagnetic waves. Internal and external means may be combined as well as desired. So, for example, an internal generic type of identification may be inserted when the medicine is formulated, and when refined into pill form, an external, patient specific type of information may be applied.

Information in various embodiments may be machine readable, or both user and machine readable. For example, bar coding techniques may be used in a machine readable embodiment, to provide appropriate information. As another example, certain information may be present in machine readable form and other information present in user readable form on the same pill.

A reader for information may be any suitable mechanism. A reader may be provided to any number of entities as desired, e.g., manufacturer, dispenser, patient, etc. Of course, one or more entities may use a reader, and some may use a reader and writer in order to both read and/or write and/or modify pill information.

It should be noted that information may also be present on a package for a pill, in addition to information on the pill. For example, rice paper wrapping or other suitable disposable and/or edible packaging may be marked.

Generally, a suitable marking mechanism is provided that will adequately convey the information to be desired. For example, generic information may be fairly simple, and so a first marking mechanism adequate to convey simple information may be used, such as a one dimensional bar code. Such information can then be used to dispense the pills in generic fashion, such as when they are sent to a pharmacy. Patient specific information may be more complicated, and so a second marking mechanism may be used, such as a two dimensional bar code or a pill wrapping.

A pharmacy, for example, may desire to add to the manufacturer's marking (in the example immediately above) patient specific marking, such as scheduling information. In this scenario, the manufacturer's markings will be machine readable, by a dispensary at the pharmacy, so that the pills are appropriately dispensed as well. The marking by the pharmacy may be either or both machine or user readable, so that the patient may be able to either use a local dispenser which reads the machine readable information, or read the information. (Of course, in this and other embodiments, it may be desired to modify the patient's information once it is placed on the pill if necessary, and so suitable marking should be used in those embodiments.)

It should be noted that information may be applied that is an indicator or other short form. For example, information may be applied to a pill that is an index to a database entry on an external pill reader or other suitably accessible device. Thus, the information need only be appropriately linked to that index in order to be read and disseminated to the client, such as through a printed sheet, packaging, etc. An embodiment uses an index, for example, by accessing a database in any suitable manner, and so provides the ability to read and, if desired, disseminate the information present in the database. As is further described below, in preferred embodiments, that database provides an individualized pharmacopoeia for a patient.

In preferred embodiments, therefore, information that has been present on a pill container, whether patient specific or generic, or both is transferred to the pill. The information may be transferred directly, such as when all the information is contained on the pill, or at least partially, such as when a pointer is transferred onto a pill for subsequent linkage to a database or the like. In various embodiments, information may be further customized so as to be suitable for the nature of the pill, e.g. a smaller pill may have only a pointer for a database link, a larger pill may have sufficient information to make an index unnecessary, etc.

It should be noted that various embodiments may also provide for updating. So, for example, if newly discovered information regarding pill safety or interactions or other information is made available, a database or other suitable means on the reader may be updated, and the user notified. Notification may be by any suitable means, such as when the user applies for a refill, when a scan of a pill is done, by a connection from a reader or other device and/or database to another patient communications channel (e.g., telephone, pager, email, physician, pharmacist, etc.)

In various embodiments, information may also be used to package pills in any suitable manner and/or means for a patient. For example, embodiments may provide multiple pill packages for a patient, that is, a packaging system providing all the medications for a patient to be taken at various intervals.

In certain preferred embodiments, an individualized pharmacopoeia may be provided. For example, information may be individualized for a particular patient at a manufacturer or pill dispensary, and the pills dispensed to the patient. So, for example, a pharmacist may be able to access a patient medication database, providing information on all pills for a patient, and assemble pills appropriate to a patient and/or a patient's schedule. A printed or other schedule may also be provided.

Embodiments may be especially useful for the disabled or other impaired individuals, who may not be able to take the medicine on schedule without help. Thus, various embodiments may provide for individualized delivery of a pill.

Packaging may occur using any suitable automated and/or manual means. For example, embodiments may provide a series of packages with appropriate dosages for various times for the user, e.g., one for pills to be taken at breakfast, one for pills to be taken at lunch and one for pills to be taken at supper.

Figure 2:
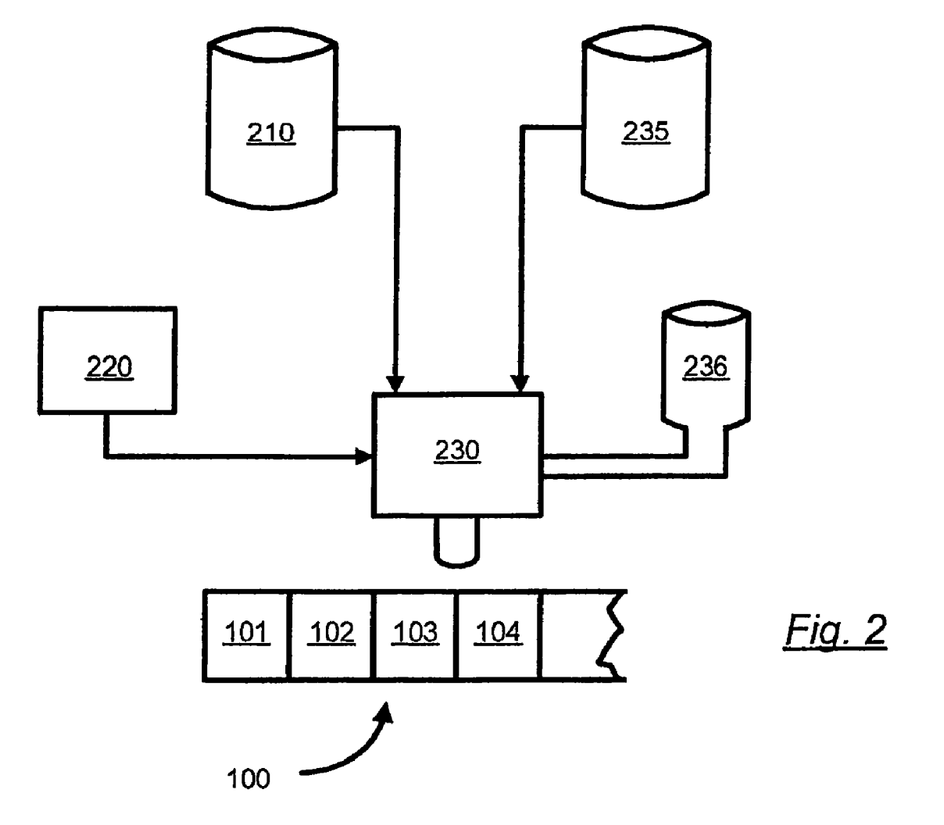
FIG. 2 shows a preferred embodiment.

Turning to FIG. 2, an embodiment is seen for individualized multiple pill management. Patient A receives a dispenser shown generally at 100. Subpackage 101 comprises pills to be taken at breakfast; Subpackage 102 comprises pills to be taken at lunch; Subpackage 103 comprises pills to be taken at dinner; Subpackage 104 comprises pills to be taken at bedtime, etc.

Package 100 is assembled by Pill Provider 220, which may be automated, manual or a combination of both. Pill Provider 220 accesses database 210 as desired. Database 210 provides information on suitable medicine, and its scheduling, for patient A. Information for the database may come from one source, e.g., HMO's, hospitals, primary health care providers, or other suitable sources, or more than one source, e.g., HMO's, hospitals, primary health care providers, or other suitable sources, and is stored in database 210 as is known in the art.

Pill Provider 220 accesses dispensary 230 as desired as well. Dispensary 230 contains one or more types of pills, such as shown in container 236, labeled as is desired with information as is desired, and is linked to a database 235 that provides pill information, so that dispensary 230 may read a pill and consult its database in order to understand the information on the pill.

Dispensary 230 reads patient A's information from database 210 and also reads or has read pill information from database 235. The appropriate pills for patient A are accessed via reading information on pills accessed by dispensary 230 and are dispensed from dispensary 130, into subpackages 101, 102, 103, 104, etc. Each subpackage is sealed as is known in the art, after assembly.

Figure 3:
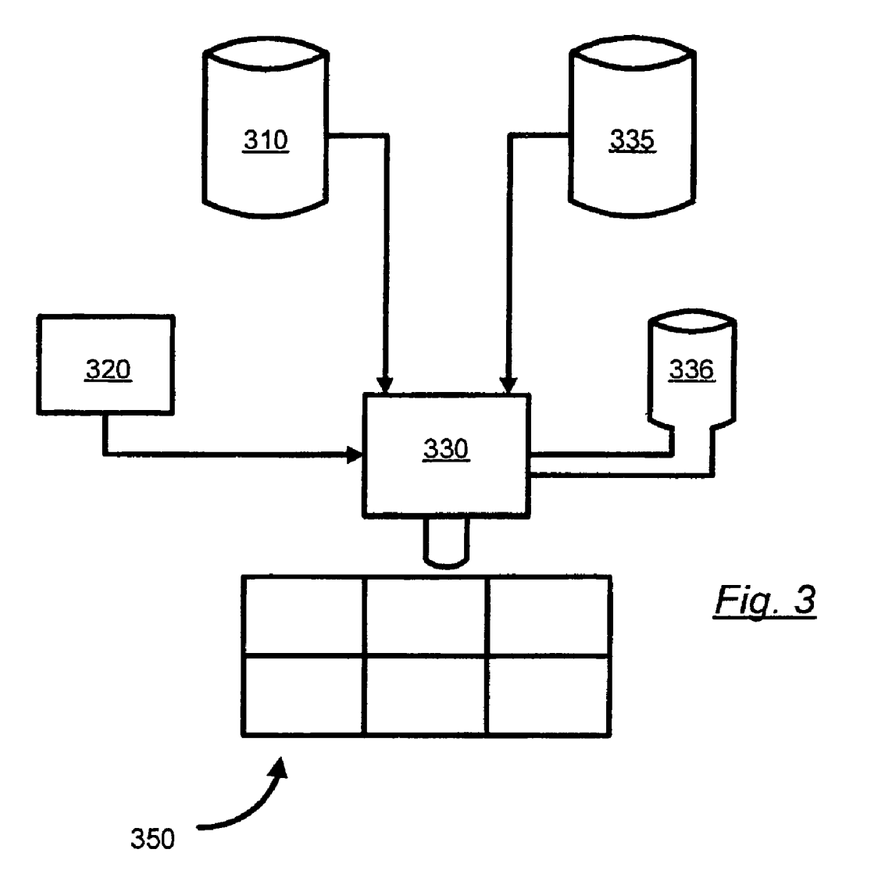
FIG. 3 shows a preferred embodiment.

FIG. 3 shows an example of another embodiment for individualized multiple pill management. Database 310 provides information on suitable medicine for patient B. Information for the database may come from one source, e.g., HMO's, hospitals, primary health care providers, or other suitable sources, or more than one source, e.g., HMO's, hospitals, primary health care providers, or other suitable sources, and is stored in database 310 as is known in the art.

Pill Provider 320, which may be automated, manual or a combination of both, accesses database 310 as desired. Pill Provider 320 accesses dispensary 330 as desired as well. Dispensary 330 contains one or more types of pills, such as shown in container 336, labeled as is desired with information as is desired, and is linked to a database 335 that provides pill information, so that dispensary 330 may read a pill and consult its database in order to understand the information on the pill.

Dispensary 330 reads patient B's information from database 310 and also reads or has read pill information from database 335. The appropriate pills for patient B are accessed via reading information on pills accessed by dispensary 330 and are dispensed from dispensary 330, into dispenser 350.

Figure 4:
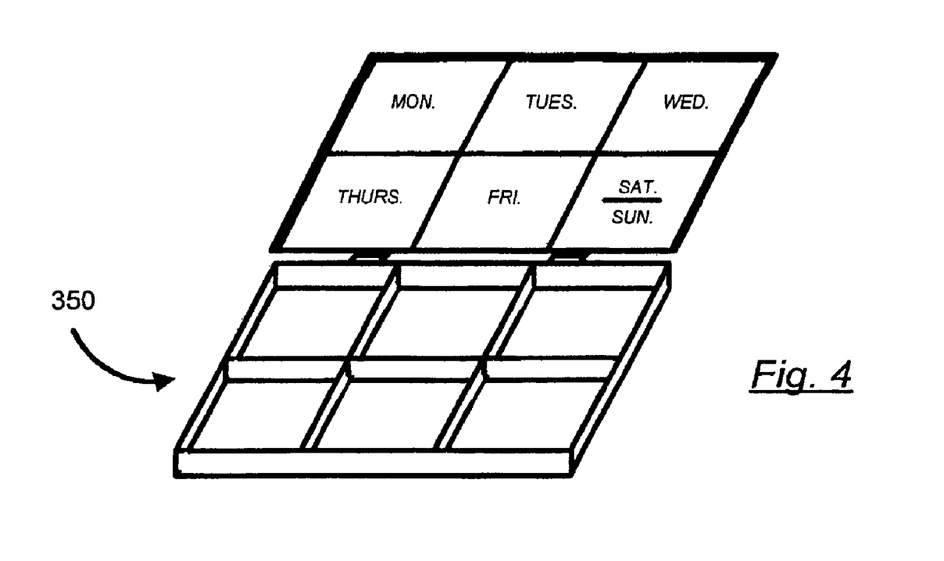
FIG. 4 shows a preferred embodiment.

Turning to FIG. 4 for a moment, an embodiment of dispenser 350 is shown. Dispenser 350 is divided into days of the week. Thus, returning to FIG. 3, dispensary 330 dispenses the appropriate medications for patient B into the appropriate day of the week divisions of dispenser 350.

Dispenser 350 is then provided to patient B, who now has a dispenser for his or her medicine with appropriate day of the week indications. Thus, in this and other embodiments, a patient's medicine may be conveniently scheduled. Of course, scheduling may be according to any desired schedule, in any desired time increments, such as days of the week, dates, times of days, weeks, months, etc.

Embodiment that provide individualized patient management may use a database of patient medications. Such a database includes patient specific information, as had been described above. It may be populated and accessed using any suitable means. So, for example, a pharmacist may access such a database and accordingly assemble a patient specific medicine or medicines, delivered in any suitable means.

A separate notification device and/or system may also be provided. For example, a patient may be notified by any suitable means to take his or her medication. Such notification may be triggered through a database link, such as a link to database 310 in FIG. 3, which also provide reminders as desired, e.g., to a patient telephone, cell phone, pager, etc.

Certain embodiments may provide alerts and/or alarms in a dispenser as well, in order to set and/or provide alerts and/or alarms to a user. For example a dispenser may provide an alert to a user at intervals to take a pill, in order to alert a user of a scheduled time for the taking of said pill. As another example a user may configure an alarm in order to provide future alerts for the taking of a pill.

One preferred embodiment provides customized dispensing for pills for hospital or other health care facilities' use. Health care facilities may have to track medicine for a number of patients and the use of a patient specific customization system and/or apparatus may be helpful So, for example, a hospital may be supplied with pills with generic information, which it can then machine read and dispense to the appropriate patients. Customized packaging may be used as well. Embodiments may use packaging for example that is suitable for visually or otherwise impaired patients, so as to make it more convenient for a patient to determine what pills to take and when. Embodiments may assist in actually permitting pills to be picked up and ingested, for example, when a patient may have difficulty with smaller pills, etc.

Customized pill formation may be used as well. Embodiments may allow for medicine resizing and/or reformulation according to patient abilities. For example, a patient may be unable to take medicine according to a standard pill size of the medicine, such as a pill size that is too large for the patient, too small, etc. It may be possible therefore to assemble a pill, once the medicine information is provided, into a pill size that is more accessible to the patient. Thus a dispenser may substitute one size for another with appropriate information.

Yet other embodiments provide a security system for tracking medicine. Pills may be tracked according to their information. For example, an embodiment with personal information, if lost by the patient and found by another, may be tracked to the user by reading the information present on the pill. As another example, a law enforcement or other agency may track pills back to an original patient, thus possibly limiting misuse, e.g., resale, of controlled substances.

Information provided by any dispensers and/or readers may be useful as well. For example, billing records may be generated, insurance records may be kept, refills scheduled, notices provided to a patient, automated management of medicines provided, etc.

Embodiments may also reduce errors in pill dispensing. For example, pharmacies may be able to ensure that scheduled medicines are not counter indicated, physicians maybe able to ascertain that medicine combinations are effective, etc.

Any such information included herein may be, if desired, provided so as to be sufficiently protected according to appropriate regulations, e.g., privacy regulations and the like, using any suitable means.

The above description and the views and material depicted by the figures are for purposes of illustration only and are not intended to be, and should not be construed as, limitations on the invention.

Figure 5:
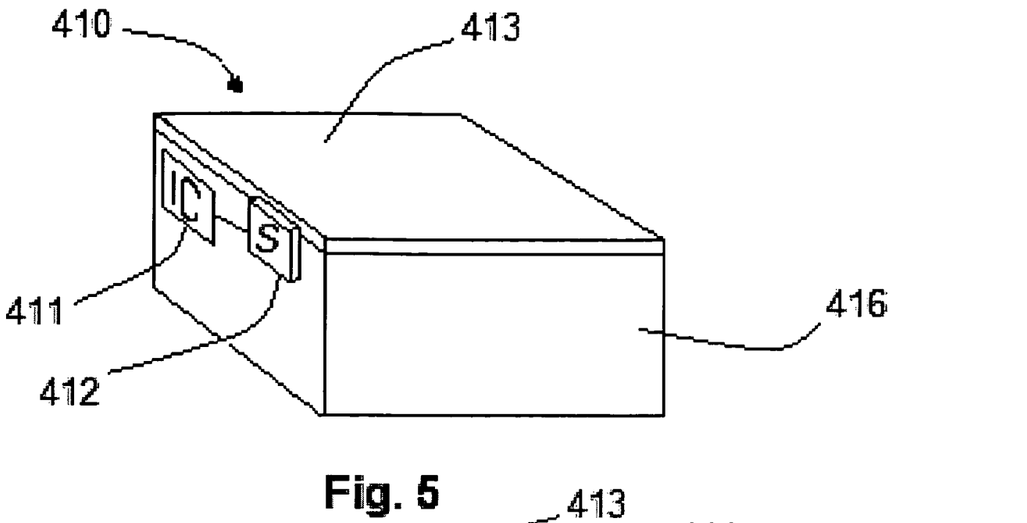
FIG. 5 illustrates a front perspective view of an alternate embodiment of a pill dispenser according to the invention.
Figure 6:
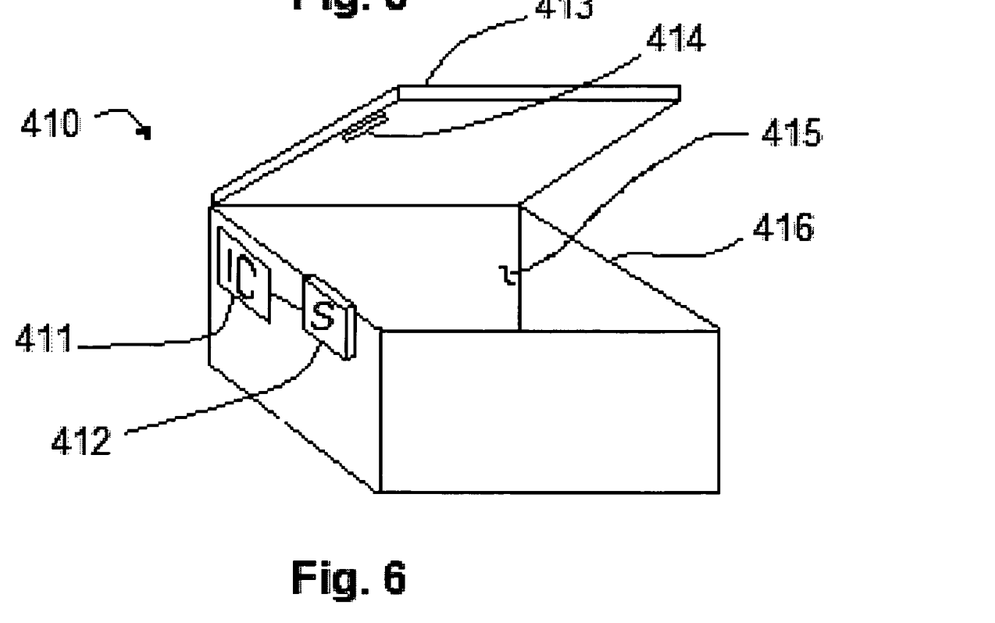
FIG. 6 illustrates a perspective view showing the pill dispenser of FIG. 5 with the cover in an open position.

An alternate embodiment of the invention is illustrated in FIGS. 5 and 6, including a dispenser 410 for medicine, the dispenser 410 having an integrated circuit 411 and a sensor 412. The dispenser is shown having a body portion 416 and a cover or cap 413. The sensor 412 may be associated with pill accession, such as, for example, an attempt to remove medication from a pill dispenser 410. For example, according to one embodiment, the pill dispenser 410 may have a cap 413. The cap 413 may be associated with a sensor 412 such that the removal or lifting of the cover 413 is sensed, and may create a sensed event. The cover 413 or other actuating element associated with the cover 413, such as, for example, a conductive contact (not shown), or non-conductive segment (not shown), may regulate the circuit activity. A change in condition of the cover 413, from closed to open (or, for example, from locked to unlocked positions where the cover 413 may still be covering the dispenser opening 415 on but moved from its locked position), for example, may trigger the sensor 412. The integrated circuit 411 preferably includes a clock. The clock may be programmed with information, including for example, an expiration date of the medication contents held within the pill dispenser 410. The integrated circuit clock may be set to a first condition event which is a date prior to the expiration date, and a second condition event which is on or after the expiration date of the medicine. Alternately, the integrated circuit clock may be programmed with a threshold triggering event which, for example, may be the expiration date of the dispenser contents. The integrated circuit 411, according to some embodiments, may include a prerecorded, or a generated voice assembled message, which is communicated through an audible medium, such as, for example, a speaker which also may be included with or as part of the integrated circuit 411. The message may, for example, be an "out of date, do not use" phrase where the clock condition threshold is met. The audible message may contain a tone or sound as well as, or alternately, an audible speech component including at least one language component. The language component may be in one or more languages (e.g., English, Spanish, or the like) and may be preselected, or may have a user selection option.

According to one example, the pill dispenser 410 may be opened thereby actuating the sensor 412 to sense an event. The sensed event (e.g., the opening of the dispenser 410) may be relayed to the integrated circuit clock. The clock may include a first circuit path, where no further event is prompted, and a second circuit path which may be closed after the expiration date is reached, so that on or after the expiration date, the circuit path associated with the sensor relay of an open event causes the generation of the audible message "out of date, do not use". In the case of a blind or visually impaired individual, the pill dispenser 410 facilitates communication of information through an audible medium.

The "out of date" message is one example of a feature of the audible pill dispenser embodiment. Alternately, or in addition thereto, audible alerts may be generated for prompts reminding one that it is time to take the pill. According to a preferred embodiment, where the pill dispenser includes sub packages, and including embodiments where each subpackage contains a pill or allotment of pills to be taken at a designated time or day, the message may be coordinated to identify the subpackage location that contains the pills to be taken. For example, "take the pills at unit D2", or "take the pills at blue", where a color is designated for a subpackage.

According to preferred embodiments, audible messages may be generated as a function of the clock. In addition, an audible message may be generated as a function of the pill inventory, which is the contents of the pills in the pill dispenser. Pill dispenser embodiments and the method of medicine management may track the number of pills in a pill dispenser, and continue to monitor and track the number as pills are removed from the dispenser. The tracking and removal of pills may be accounted as a function of time. Time generated alerts may be provided where the pill number is in excess at or past the scheduled time for taking the pill. A first message may be generated as a reminder message where the pill has not been taken (where the time threshold is about to be met), and a second message may be generated where the time threshold is met (or exceeded) and the pill dispenser has not been opened, and/or the pill inventory has not changed (e.g., reduced by the dosage amount).

According to an alternate embodiment, the pill may include information provided thereon. The information may be provided using any one or more of the following techniques: printing; engraving; masking; ion deposit means; surface modification means; internal doping means; or covering said pill with an edible covering. The information may be read with a reader, including the sensor 414 which may be configured to read pill information. According to a preferred embodiment, the pill or package, such as, for example, rice paper covering the pill, may be sensed as it is removed from the container. For example, the sensor 414 may include means for reading or sensing the pills or pill covering. Each pill may generate, itself or through its covering, a detectible attribute so that information, such as, for example, the inventory of pills in the dispenser, may be derived.

According to an alternate embodiment, a dispenser or container is provided and is constructed from a material which includes a barrier layer, or, according to the embodiments, includes a material that is impregnated into the dispenser structure to facilitate storage of contents, such as, for example, pills contained therein. The life of pharmaceuticals, such as, for example, pills, has certain time limitations, as pills often are subject to degradation, deterioration, or a change of chemical composition. These effects may gradually take place over a time period, and are accelerated by exposure to potential spoiling contaminants, such as, for example, oxygen, moisture, light, temperatures and temperature changes.

The dispenser of the preferred embodiments may be constructed from a plastic material. According to one preferred embodiment, the dispenser material is dyed or otherwise colored to be a dark color, such as brown or black, and according to some preferred embodiments, preferably may be opaque. According to another embodiment, the dispenser material may include a chemical which does not allow oxygen to enter the dispenser. For example, the dispenser may be constructed from a plastic which is doped with a chemical that prohibits or minimizes oxygen entry into the dispenser. According to preferred embodiments, the chemical may be provided as part of the dispenser composition, or alternately, or, in addition thereto, may be applied to the dispenser as a coating. For example, an oxygen barrier coating may include resins and films, such as, for example, polyvinylidene chloride (PVDC) resins and films, including for example, materials available under the trademark SARAN. According to preferred embodiments, the film may be applied in a liquid form, as is well understood by those skilled in the art. Examples of film application may include spraying, immersing, fusing, molding or forming with or as part of the dispenser. A coating material, according to some embodiments, may be applied to the dispenser to provide a protective barrier that prevents or minimizes oxygen entry into the dispenser, and may be also include a color shading. The color may be selected based on interactions of the potential pharmaceutical or pill content, such as, using a yellow shading to absorb or otherwise limit passage of ultra violet light (which may degrade certain products). According to alternate embodiments, coatings may include materials selected from the group consisting of ethylene-vinyl acetate polymers and polymers of vinylidene chloride. The materials may be blended with other compounds, such as, for example, butyl rubber. According to other embodiments, in addition to SARAN brand films, the dispenser may be provided with an interior or exterior coating that is formed from an oxygen barrier film made of Nylon brand plastic, polyethylene vinyl alcohol plastic, or other films, including single or multilayer films that have as a component thereof an oxygen barrier plastic.

According to embodiments of the invention, a pill system is provided to facilitate increased shelf-life and improved storage of pharmaceuticals. The configuration of individually packaged dispensers or containers, including where one or multiple pills are packaged, prevents or minimizes the exposure of the pills that are not to be taken at that time. For example, where a dispenser contents of traditional type dispenser includes several pills of the same type, and one is to be taken daily, the dispenser must be opened at least once a day, thereby subjecting all of the pills to the conditions of oxygen, moisture and other potential contaiminants. Over time, as the pill contents in the dispenser are removed, the pills remaining in the container the longest, have the greatest exposure to repeated potential contaiminants. For example, desiccants may be expended during the first opening, or first couple of openings, thereby rendering the remaining pills the potential reactants for subsequent moisture exposures. The effect may be to reduce effectiveness or the expected dosage amount of the exposed pills. For example, where a body function is regulated by an effective amount of medicament in a pill, where the medicament is subjected to narrow tolerances, the expiration dates may be very short. The invention provides embodiments which provide packaging for pills where deleterious effects, such as moisture and prolonged oxygen exposure, are eliminated or minimized. For example, according to embodiments of the invention, the pills may be stored in a package for one-time use, as described herein in conjunction with other embodiments of the invention. The package, according to preferred embodiments, may include information that is printed or encoded on the pill or on packaging for the pill, including, for example, the information discussed herein in connection with the embodiments of the invention. The information may be provided, for example, as shown and described herein, including by printing; engraving; masking; ion deposit means; surface modification means; internal doping means; or covering said pill with an edible covering.

Figure 7:
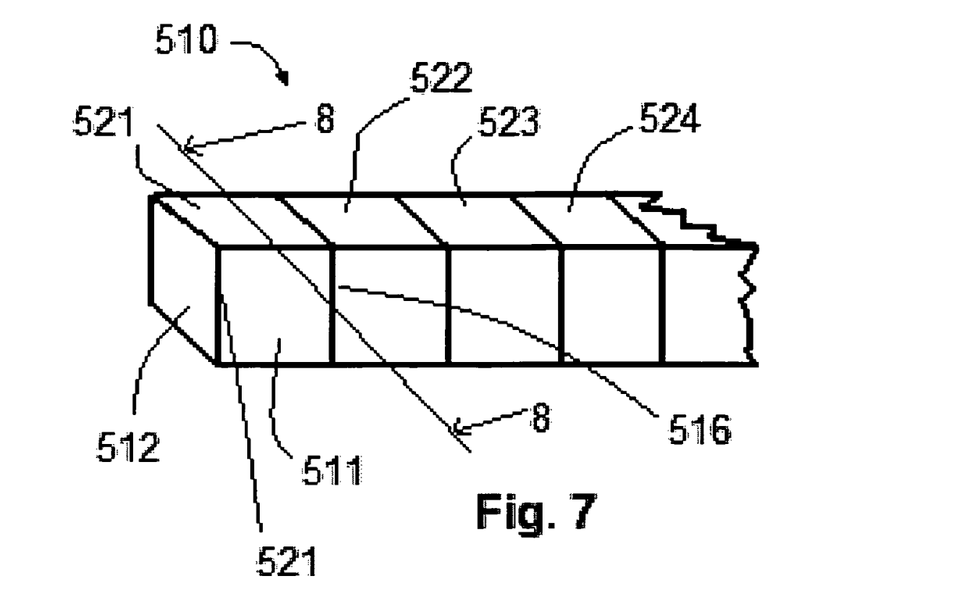
FIG. 7 illustrates another alternate embodiment of a pill dispenser according to the invention, illustrated with a barrier.
Figure 8:
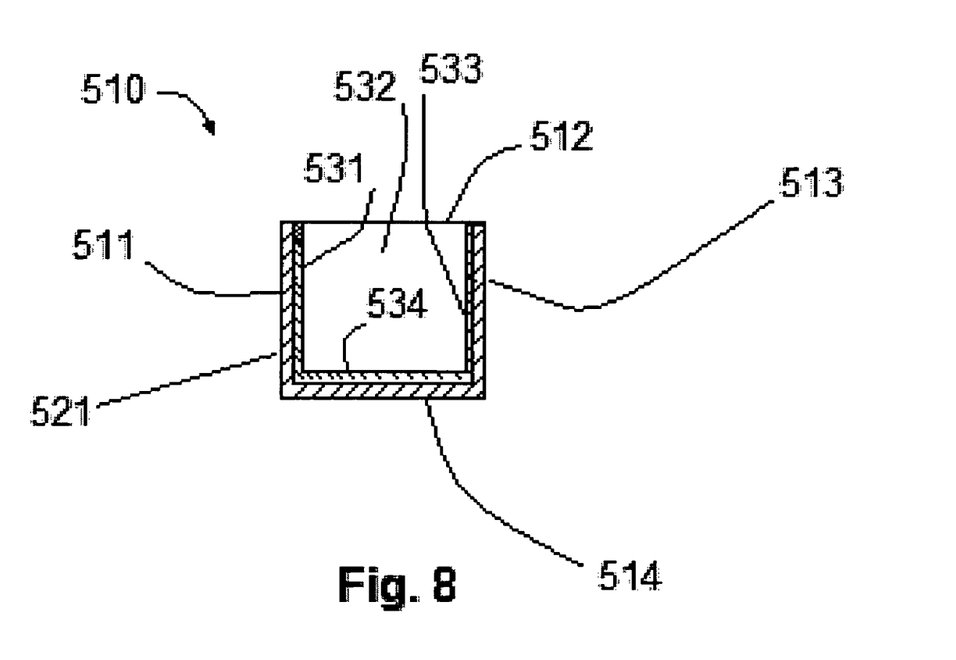
FIG. 8 is a sectional view of the dispenser of FIG. 7, taken through the line 8-8 of FIG. 7, and showing the first subpackage separate from the remainder of the dispenser.

Preferred embodiments provide a package that includes an oxygen barrier. Where package embodiments provide a sub package or compartments for each dosage allotment (such as, for example, a group of pills to be taken at the same time, e.g., Monday at 8:00 a.m.) each dosage unit may be packaged in its own barrier separate from other dosage units, including dosage units that may be part of the same pill dispenser unit. A barrier layer or impregnated material may be applied in conjunction with the individualized multiple pill management. For example, referring to the subpackage dispenser 100 shown in FIG. 2, the barrier may be provided (impregnated into or as a layer) to envelope each subpackage 101, 102, 103, 104, separately from the others, so that even by accessing one subpackage (e.g., 101, 102, 103, 104) the other subpackages not accessed remain barriered. FIGS. 7 and 8 illustrate an exemplary embodiment of a pill dispenser 510 shown having an enclosure including side walls 511, 512, 513, 516 a bottom 514 and a cover 515 defining at least one subpackage or pill compartment. The pill dispenser 510 is illustrated having a configuration with a plurality of compartments or subpackages 521, 522, 523, 524, each of which may be constructed in accordance with the description of the first compartment or first subpackage 521. Optionally, the subpackages 521, 522, 523, 524 may share one or more common walls between them, such as, for example, the wall 516 between adjacent subpackages 521 and 522. The pill dispenser 510 is illustrated including barrier layers 531, 532, 533 provided, respectively, on the side walls 511, 512, 513, barrier layer 534 on the bottom 514, with the barrier layers on the cover 515 and side wall 516 not being shown in the drawing views. Barrier layers may, for example, be constructed from the materials mentioned herein. While the barrier layer is described as a plurality of layers, the barrier layer may be a continuous layer. While the drawing FIGS. 7 and 8 illustrate an exemplary embodiment, the barriered dispenser 510 may be provided with a sensor and integrated circuit, as discussed herein, and, for example, may include the features described and illustrated in connection with FIGS. 5 and 6.

Moreover, certain modifications or alternatives may suggest themselves to those skilled in the art upon reading of this specification, all of which are intended to be within the spirit and scope of the present invention as defined in the attached claims.

What is claimed is:

1. A method for medicine management comprising:
providing information on a pill; and,
providing a reader for said information,
where said providing information is done using a technique selected from a group consisting essentially of: engraving; masking; ion deposit means; surface modification means; internal doping means; or covering said pill with an edible covering;
wherein said internal doping means consists of doping with appropriate inert substances that reflect electromagnetic waves, and
wherein when said providing information consists of internal doping means said reader is configured to read electromagnetic waves,
wherein covering said pill consists of covering said pill with rice paper and wherein information is provided on said rice paper, said rice paper and information thereon being ingestible; and
further including providing a pill dispenser,
wherein said reader is configured with said pill dispenser to read said information that is provided on said pills, information that is provided on said rice paper covering said pill, or information provided on both.

2. The method of claim 1, wherein said reader is operably linked with an audible circuit to generate an audible message.

3. The method of claim 2, wherein said pill dispenser includes a cover, and wherein said audible circuit includes a sensor that senses the opening and closing of said pill dispenser cover.

4. The method of claim 2, wherein said audible circuit includes a clock, and wherein the pill information includes an expiration date, and further including generating an audible message upon the occurrence of both the expiration date having been reached and the cap having been opened.

5. The method of claim 2, wherein said audible circuit includes a clock, and the method includes determining an inventory of pills in said container.

6. The method of claim 5, wherein said audible message is generated as a function of said clock and said determined pill inventory.

7. The method of claim 1, including sensing means provided on said dispenser to sense pill information.

8. The method of claim 7, wherein said reader comprises said sensing means.

9. The method of claim 7, wherein said sensing means comprises a sensor operably configured with said dispenser.

10. A method as in claim 1, wherein said information is selected from the group consisting essentially of: the name of the medicine, the dosage embodied in the pill, lot number, serial number, manufacturer name, physician information, or medical condition information.

11. A method as in claim 1, comprising modifying said information.

12. A method as in claim 1, wherein said information is coded.

13. A method as in claim 12, wherein said information is bar coded.

14. A method as in claim 1, further comprising dispensing said pill from a dispenser with audible message generating means.

15. A method as in claim 14, further comprising configuring said audible message generating means to provide an alert to a user in order to alert said user of a scheduled time for the taking of said pill, where the alert comprises audible speech containing at least one language component.

16. The method of claim 1, wherein said reader is operably linked with an audible message circuit to generate an audible message.

17. A method for managing medicine, comprising: reading information on a pill via a reader; and, delivering a pill, the method further including:
providing a database containing information including suitable medicine and its scheduling for a patient,
providing a dispensary containing one or more types of pills wherein said one or more types of pills are labeled with information, and wherein said dispensary is linked to a database containing information corresponding to the information on the pill;
reading with said dispensary said information on said pill, and
correlating said information on said pill with said database containing information including suitable medicine and its scheduling for a patient;
accessing appropriate pills for the patient based on correspondence of said pill information by reading information on pills; and
dispensing from said dispensary said pills into one or more subpackages of a dispenser, wherein each subpackage is associated with a scheduling event, and
sealing said subpackages,
wherein said subpackages include a barrier to exclude contaminants from entry therein.

18. The method of claim 17, wherein each said subpackage includes at least one wall, and wherein said barrier comprises a chemical impregnated within said wall.

19. The method of claim 18, wherein said chemical is doped in said subpackage composition.

20. The method of claim 19, wherein said chemical doping is accomplished by doping said subpackage composition with one or more compounds selected from the group consisting of: polyvinylidene chloride (PVDC) resins.

21. The method of claim 17, wherein said barrier includes a layer comprising at least one compound selected from the group consisting of: ethylene-vinyl acetate polymers, polymers of vinylidene chloride, butyl rubber blends, SARAN brand films, Nylon plastic and polyethylene vinyl alcohol plastic.

22. The method of claim 17, including providing a barrier comprising a single or multilayer film that has as a component thereof an oxygen barrier material.

23. The method of claim 17, wherein the barrier comprises providing a subpackage having an opaque color.

24. The method of claim 17, wherein said dispenser includes an audible message generating circuit;
and generating an audible message as a function of the scheduling of said medicine.

25. The method of claim 24, wherein generating an audible message includes generating a reminder message that the medicine should be taken.

26. The method of claim 24, wherein generating an audible message includes generating a reminder message that the medicine is out of date.

27. The method of claim 24, wherein said message generating circuit includes a clock, and wherein said audible message is operably linked with one or the other or both of said database information and said information on said pill.

28. The method of claim 24, wherein said dispenser includes a cover covering each subpackage, and wherein said audible message generating circuit includes a sensor that senses the opening and closing of a subpackage cover.

29. The method of claim 28, wherein said audible message generating circuit includes a clock, and wherein the one or the other or both of said database information and said information on said pill includes an expiration date, the method including generating an audible message upon the occurrence of both: the expiration date having been reached and a subpackage cover having been opened.

30. The method of claim 24, wherein said audible message generating circuit includes a clock, and the method includes determining an inventory of pills in said dispenser.

31. The method of claim 30, wherein determining an inventory of pills in said dispenser includes determining an inventory of pills in a subpackage.

32. The method of claim 30, wherein said audible message is generated as a function of both said clock and said determined pill inventory.

33. A method as in claim 17, wherein said information is selected from the group consisting essentially of: the name of the medicine, the dosage embodied in the pill, lot number, serial number, manufacturer name, physician information, or medical condition information.

34. A method as in claim 17, comprising providing said information.

35. A method as in claim 34, where said providing is done using a technique selected from a group consisting essentially of: printing; engraving; masking; ion deposit means; surface modification means; or internal doping means.

36. A method as in claim 17, wherein said information is coded.

37. A method as in claim 36, wherein said information is bar coded.

38. A method as in claim 17, further comprising dispensing said pill from a dispenser having audible message generating means.

39. A method as in claim 38, further comprising configuring said audible message generating means to provide an alert to a user in order to alert said user of a scheduled time for the taking of said pill.

40. A method for managing medicine, comprising: reading information on a pill via a reader; and, delivering a pill, the method further including:
   providing a database containing information including suitable medicine and its scheduling for a patient,
   providing a dispensary containing one or more types of pills wherein said one or more types of pills are labeled with information, and wherein said dispensary is linked to a database containing information corresponding to the information on the pill;
   reading with said dispensary said information on said pill, and
   correlating said information on said pill with said database containing information including suitable medicine and its scheduling for a patient;
   accessing appropriate pills for the patient based on correspondence of said pill information by reading information on pills; and
   dispensing from said dispensary said pills into one or more subpackages of a dispenser, wherein each subpackage is associated with a scheduling event, and
   sealing said subpackages;
   wherein said dispenser includes an audible signal generating circuit;
   and generating an audible signal as a function of the scheduling of said medicine.

41. The method of claim 40, wherein said audible signal comprises an audible message.

42. A method for medicine management comprising: providing information on a pill; and, providing a reader for said information, where said providing is done using a technique selected from a group consisting essentially of: engraving; masking; ion deposit means; surface modification means; internal doping means; or covering said pill with an edible covering; wherein said internal doping means consists of doping with appropriate inert substances that reflect electromagnetic waves, and wherein when said providing information consists of internal doping means said reader is configured to read electromagnetic waves;
   where said providing is done using at least two techniques, wherein one of said at least two techniques consists of internal doping means consisting of doping with appropriate inert substances that reflect electromagnetic waves, and wherein said at least one other of said at least two techniques is selected from the group consisting essentially of: printing; engraving; masking; ion deposit means; surface modification means; internal doping means; or covering said pill with an edible covering; and
   wherein said at least one technique provides information selected from at least one of the group consisting essentially of: the name of the medicine, the dosage embodied in the pill, lot number, serial number, manufacturer name, physician information, or medical condition information, and
   wherein the said at least one other of said at least two techniques provides information selected from at least another one of the group consisting essentially of: the name of the medicine, the dosage embodied in the pill, lot number, serial number, manufacturer name, physician information, or medical condition information; and
   wherein said reader is operably linked with a message circuit, and wherein the method further includes generating an audible message associated with one or more attributes of said pill information.

43. The method of claim 42, wherein covering said pill consists of covering said pill with rice paper and wherein information is provided on said rice paper, said rice paper and information thereon being ingestible.

* * * * *